United States Patent
Kikuchi et al.

[11] Patent Number: 5,947,975
[45] Date of Patent: Sep. 7, 1999

[54] INSERTING DEVICE FOR DEFORMABLE INTRAOCULAR LENS

[75] Inventors: Toshikazu Kikuchi, Hachioji; Toshiyuki Nakajima, Matsudo; Kenichi Kobayashi; Takashi Masuda, both of Tokyo, all of Japan

[73] Assignee: Canon Staar Co., Inc., Tokyo, Japan

[21] Appl. No.: 09/032,211

[22] Filed: Feb. 27, 1998

[30] Foreign Application Priority Data

| Mar. 7, 1997 | [JP] | Japan | 9-053503 |
| Mar. 10, 1997 | [JP] | Japan | 9-055139 |
| May 13, 1997 | [JP] | Japan | 9-122373 |
| Jan. 16, 1998 | [JP] | Japan | 10-006300 |

[51] Int. Cl.$^6$ ..................................................... A61F 9/00
[52] U.S. Cl. .................. 606/107; 606/108; 606/138; 623/4; 623/6; 609/15
[58] Field of Search ............................... 606/107, 108, 606/138; 623/4, 6; 604/15

[56] References Cited

U.S. PATENT DOCUMENTS

| 4,573,998 | 3/1986 | Mazzocco . | |
| 4,681,102 | 7/1987 | Bartell . | |
| 5,098,439 | 3/1992 | Hill et al. . | |
| 5,190,552 | 3/1993 | Kelman . | |
| 5,496,328 | 3/1996 | Nakajima et al. | 606/107 |
| 5,616,148 | 4/1997 | Eagles et al. | 606/107 |

FOREIGN PATENT DOCUMENTS

| 58-146346 | of 1983 | Japan . |
| 5-103803 | of 1993 | Japan . |
| 5-103808 | of 1993 | Japan . |
| 5-103809 | of 1993 | Japan . |
| 7-23990 | of 1995 | Japan . |
| 7-23991 | of 1995 | Japan . |

*Primary Examiner*—Michael Buiz
*Assistant Examiner*—Lien Ngo
*Attorney, Agent, or Firm*—Ladas & Parry

[57] ABSTRACT

An insertion device for inserting a deformable intraocular lens into the eye. The insertion device has a an enclosing member that is attached to the body of the insertion device and that has two hinge portions at a lens receiving section. Further, a retainer member is fitted onto the enclosing member and a holder fitted onto the body. The deformable intraocular lens is placed in the lens receiving section after the enclosing member is opened. When the holder is retracted, the intraocular lens is deformed by a tapered inner wall portion formed at a the tip end of the holder, so that the exterior size of the lens is reduced. Subsequently, a push rod supported by the body is advanced in order to insert the lens into the eye.

12 Claims, 13 Drawing Sheets

INSERTING DEVICE FOR DEFORMABLE INTRAOCULAR LENS

BACKGROUND OF THE INVENTION

1. Field of the Invention

The present invention relates to an insertion device for inserting a deformable intraocular lens into the eye. Examples of such a deformable intraocular lens include a deformable intraocular lens that is inserted into the eye in place of the natural lens when the latter is physically extracted because of cataracts, and a vision correction lens that is inserted into the eye for the sole purpose of vision correction.

2. Description of the Related Art:

Implantation of an intraocular lens for treating cataract has been widely performed since 1949, when Ridley implanted for the first time an artificial lens, i.e., intraocular lens into the human eye in place of an opaqued natural lens during cataract surgery.

The intraocular lens used first had an optical portion made of polymethyl methacrylate (PMMA). The implantation of the intraocular lens was accompanied by complications which occurred after the cataract surgery. Many ophthalmologists have shown interest in the complications and have studied them. As a result, most of the problems have been solved. However, since the optical portion is made of a hard material, an incision for implantation of such an intraocular lens must have a dimension somewhat greater than the diameter of the optical portion. Since an incision to be formed in the eyeball is large, in the degree of astigmatism after surgery increases due to suture of the incision.

A method of surgery has been pointed out as a cause of the above-mentioned complications. That is, the conventional surgery for extracting a natural lens because of cataract has been performed by using an ECCE (extracapsular cataract extraction) operation technique in which a lens is extracted without crushing it. Since this operation technique has required formation of an incision of about 10 mm, the operation caused astigmatism quite often. To solve this problem, a technique called pharmacoemulsification (PEA) using an ultrasonic emulsification/suction apparatus has been developed recently. In this method, an opaqued natural lens is crushed and emulsified using ultrasonic waves emitted from a cylindrical ultrasonic chip, and is sucked for extraction. When this method is used, the size of an incision formed in the eyeball can be decreased to a size sufficient for insertion of the cylindrical ultrasonic chip. A crushed lens can be extracted through an incision of about 3 to 4 mm. Therefore, this method makes it possible to perform the extraction operation by forming only a small incision, which mitigates the astigmatism after the operation. However, since the optical portion is made of a hard material, an incision for implantation of such an intraocular lens must have a dimension somewhat greater than the diameter of the optical portion, as mentioned above. In the case of a standard intraocular lens having an optical portion of 6.0 mm, an incision having a size equal to or greater than 6.5 mm must be formed. Therefore, even if an opaqued natural lens is extracted through a small incision using pharmacoemulsification, the incision must be widened so as to insert an intraocular lens. Accordingly, the problem of astigmatism occurring after surgery due to the large incision has not been solved.

In order to mitigate astigmatism after surgery, improved intraocular lenses have been developed which can decrease the size of incisions. Examples of such improved lenses include an intraocular lens having an oval optical portion which is inserted into an incision such that its smaller radius is oriented in the direction of the incision, and an intraocular lens with an optical portion having a reduced diameter. However, each of these intraocular lenses still has a hard optical portion. Therefore, employment of these intraocular lenses decreases the incision size only to about 5.5 mm (i.e., only by about 1 mm).

In order to solve the above-described fundamental problems, intraocular lenses themselves have been improved recently. Such an improved intraocular lens is disclosed in Japanese Patent Application Laid-Open (kokai) No. 58-146346. In the intraocular lens, at least an optical portion is made of a deformable elastic material having a predetermined memory characteristic. Alternatively, at least an optical portion is made of an elastic material having a predetermined memory characteristic, and supports are provided which are made of a material different from that of the optical portion and are adapted to support the optical portion within an eye. Moreover, as disclosed in Japanese Patent Application Laid-Open (kokai) Nos. 58-146346, 4-212350, 5-103803, 5-103808, 5-103809, and 7-23990 improved insertion tools have been proposed. Using these tools, the optical portion of an intraocular lens is compressed, rolled, bent, stretched, or folded so as to reduce its exterior size, thereby making it possible to insert the intraocular lens through a small incision. These intraocular lenses and insertion tools therefor make it possible to perform surgery by forming only a small incision, thereby mitigating astigmatism after surgery.

FIGS. 32 to 35 show the conventional deformable intraocular lenses. The deformable intraocular lens shown in FIG. 32 is composed of a circular optical portion 2 and two symmetrically disposed supports 3. The circular optical portion 2 is made of an elastic material having predetermined memory characteristics. The supports 3 are made of a material different from that of the optical portion 2, and the bases 3a of the supports 3 are embedded in the peripheral region of the optical portion 2 for fixing, while the wire-shaped tails 3b are curved. The optical portion 2 has on the periphery thereof projections 2a for reinforcing the positions where the bases 3a of the supports 3 are embedded. The deformable intraocular lens 1 shown FIG. 33 is configured in the same manner as is the deformable intraocular lens of FIG. 32 except that the projections 2a are omitted. Each of the deformable intraocular lenses shown in FIGS. 34 and 35 is composed of a circular optical portion 2 and a pair of thin plate-shaped support portions 4 that are integral with the optical portion 2. The optical portion 2, like the optical portion 2 shown in FIG. 32, is made of an elastic material having predetermined memory characteristics. The support portions 4 are projected from the periphery of the optical port 2 in opposite directions.

An insertion device disclosed in, for example, Japanese Patent Application Laid-Open (kokai) No. 7-23991 is used for deformable intraocular lenses, as shown in FIGS. 32 to 35, each of which is composed of the optical portion 2 and the support portions 3 or 4, of which at least the optical portion 2 has predetermined memory characteristics. The deformable intraocular lens 1 is folded in order to reduce its exterior size and is advanced along an insertion tube having, for example, a cylindrical shape, in order to be inserted into the eye through an incision formed in the eyeball.

FIGS. 26(a), 26(b) and 27 show the structure and operation of the conventional insertion device. First, an enclosing member 5 of the insertion device having a hinge portion 6 is opened. A deformable intraocular lens is placed on a lens receiving section 7 such that the lens engages grooves 9a and 9b. Subsequently, the enclosing member 5 is closed so as to reduce the exterior size of the deformable intraocular lens and hold it. The grooves 9a and 9b become shallower toward the insertion-tube side of the lens receiving section 7. However, the grooves 9a and 9b extend up to the rear end of the lens receiving section 7 while maintaining constant depth. Since the grooves 9a and 9b converge at the front side with respect to the direction along which the lens is pushed out, the position where the lens is to be placed can be determined with reference to the converged portions. However, since the grooved structure continues unchanged to the rear end, no reference for positioning exists at the rear side, rendering the positioning difficult. Further, when the enclosing member 5 is closed, the deformable intraocular lens placed in the lens receiving section may move rearward.

After the operation of placing the intraocular lens on the lens receiving section 7 and closing the enclosing member 5, an engagement member 15 provided on a device body 12 is moved toward the lens receiving section 7, while the closed state is maintained, so that the engagement member 15 engages the enclosing member 5 to maintain the closed state thereof.

After completion of the entire operation for setting the lens, a push rod 13 of the insertion device is advanced to push forward the deformable intraocular lens received in the enclosing member 5. As a result, the deformable intraocular lens is inserted into the eye through the tip end of a insertion tube 11 provided at the front end of the enclosing portion, which tip end can be inserted into the eye through a small incision formed on the eye ball.

However, in the conventional insertion device, a hinge portion 6 projects outward with respect to the grooves 9a and 9b formed in the lens receiving section 7. Therefore, when a deformable intraocular lens is placed on the lens receiving section 7 having such a configuration, as shown in FIG. 30, the deformable intraocular lens 1 interferes with the hinge portion 6 and curves. If the deformable intraocular lens 1 is allowed to remain in such a state for a long period of time, the lens 1 deforms with time.

Accordingly, immediately before the lens is inserted into the eye the operation of placing the deformable intraocular lens must be performed quickly, and therefore, the lens cannot be placed on the lens receiving section 7 in advance. That is, before insertion of the deformable intraocular lens into the eye, there is always required an operation for placing the lens on the lens receiving section 7. Further, during the placement operation, the lens must be precisely placed at a proper position. However, the operation for precise and quick placement of the lens at a proper position is very difficult, because the intraocular lens and the lens receiving section 7 are both very small, resulting in the problem that an imprecise placement operation causes an insertion failure, such as abnormal insertion of the intraocular lens into the eye.

Meanwhile, insertion of a lens into the eye for the sole purpose of vision correction has recently been performed as an application of the above-mentioned intraocular lens insertion technique—which has been used for treatment of cataracts. For the vision correction purpose as well, there has been developed a lens in which at least the optical portion is formed of a deformable elastic material having predetermined memory characteristics, as in the intraocular lens for cataract treatment, in order to reduce the size of an incision. The above-described insertion device can be used when the deformable vision correction lens is to be inserted into the eye through a small incision.

That is, the above-described insertion device has enabled insertion of a deformable intraocular lens, such as a deformable intraocular lens for cataract treatment or a deformable vision correction lens, into the eye through a small incision.

SUMMARY OF THE INVENTION

A first object of the present invention is to provide an insertion device for a deformable intraocular lens, which device allows an operator to omit an operation of placing a lens on an enclosing member, through an operation of engaging the peripheral edge of the lens with the enclosing member in advance.

A second object of the present invention is to provide an insertion device for a deformable intraocular lens, which device prevents movement of a lens after placement on the enclosing member and lets the operator know a location in the lens receiving section where the lens to be placed.

A third object of the present invention is to provide an insertion device for a deformable intraocular lens, which device allows simultaneous performance, for simplified operation, of two independent operations of deforming a lens and bringing the deformed lens into a held state.

In order to achieve the first object, the insertion device for a deformable intraocular lens according to the present invention has a structure in which a plurality of hinge portions provided in the enclosing member allow the peripheral edge of a deformable intraocular lens to engage the enclosing member, so that the lens can be held by the enclosing member in a state in which the optical portion of the lens substantially does not come into contact the enclosing portion.

The insertion device for a deformable intraocular lens according to the present invention may have another structure which allows the peripheral edge of a deformable intraocular lens to engage the enclosing member without use of the hinge portions and which deforms the deformable intraocular lens with movement of the lens.

In order to achieve the second object, the insertion device for a deformable intraocular lens according to the present invention has a structure in which grooves are formed in the lens receiving section of the enclosing member such that the grooves converge at the front and rear ends of the lens receiving section.

In order to achieve the third object, the insertion device for a deformable intraocular lens according to the present invention has a structure in which the operation of closing the enclosing member to deform an intraocular lens within the enclosing member to thereby reduce its exterior size and the operation of bringing the deformed lens into a held state can be performed simultaneously through a single operation; i.e., movement of a holder of the insertion device.

BRIEF DESCRIPTION OF THE DRAWINGS

Various other objects, features and many of the attendant advantages of the present invention will be readily appreciated as the same becomes better understood by reference to the following detailed description of the preferred embodiments when considered in connection with the accompanying drawings, in which:

FIGS. 16(a) and 16(b) show a main portion of an insertion device for a deformable intraocular lens according to a fifth embodiment of the present invention, wherein FIG. 16(a) is a plan view of the device with a cap member removed, and FIG. 16(b) is a bottom view of the cap member;

FIGS. 19(a) and 19(b) show an insertion device for a deformable intraocular lens according to a sixth embodiment of the present invention, wherein FIG. 19(a) is a plan view of the device, and FIG. 19(b) is a side view of the device;

FIGS. 20(a) and 20(b) show a holder used in the insertion device according to the sixth embodiment of the present invention, wherein FIG. 20(a) is a plan view of the holder, and FIG. 20(b) is a side view of the holder;

FIGS. 26a) and 26(b) show a conventional insertion device, wherein FIG. 26(a) is a plan view of the device.

FIGS. 28(a) and 28(b) show a state in which the enclosing member of the insertion device of FIG. 26 is engaged with the engagement member, wherein FIG. 28(a) is a plan view of the device, and FIG. 28(b) is a side view of the device;

DETAILED DESCRIPTION OF PREFERRED EMBODIMENTS

Figure 1:
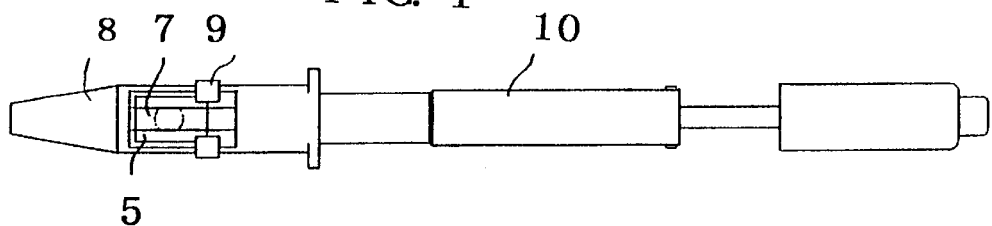
FIG. 1 is a plan view of an insertion device for a deformable intraocular lens according to a first embodiment of the present invention.
Figure 2:
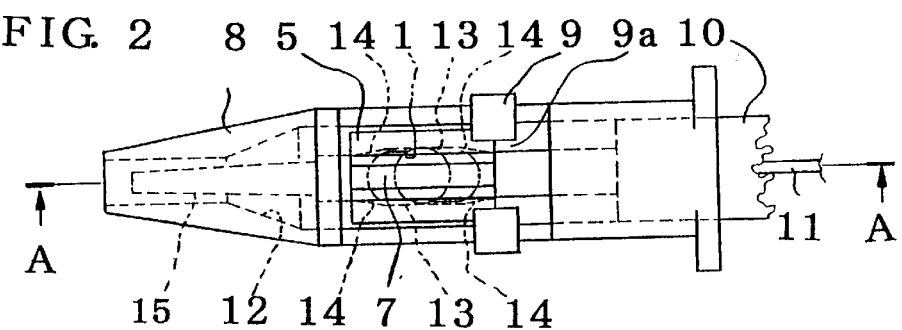
FIG. 2 is an enlarged view of a main portion of FIG. 1.

Embodiments of the present invention will be described with reference to the accompanying drawings.

FIGS. 1 to 7 shows an insertion device according to a first embodiment of the present invention. In FIGS. 1 to 7, numeral 10 denotes a body of the insertion device; numeral 1 denotes a deformable intraocular lens for cataract treatment; numeral 5 denotes an enclosing member built into the body 10; numerals 6a and 6b each denote a hinge portion provided on the enclosing member 5; numeral 7 denotes a lens receiving section which is formed upon opening of the enclosing member 5 in order to receive the intraocular lens 1, numeral 8 denotes a holder which is provided on the body 10 and is adapted to close the enclosing member 5 and maintain the closed state; numeral 9 denotes an annular retainer member for maintaining the enclosing member 5 in an opened state when the deformable intraocular lens 1 is to be placed on the lens receiving section 7; and numeral 11 denotes a push rod which is inserted into the body 10 and adapted to push out the deformable intraocular lens 1.

The cylindrical base portion 5a of the enclosing member 5 is inserted and fixed to the tip end of the cylindrical body 10. The enclosing member 5 has the lens receiving section 7 at a longitudinal center portion thereof, and an insertion tube 15 is integrally formed on the front side of the lens receiving section 7. The insertion tube 15 is tapered such that its diameter decreases toward the tip end. At a portion corresponding to the lens receiving section 7, the enclosing member 5 has a lower portion having a semicircular cross section, and a pair of quadrant-shaped upper portions connected to the lower portion via the hinges 6a and 6b. When the upper portions (i.e., the enclosing member 5) are closed, the enclosing member 5 forms a closed cylindrical shape. A groove 13 is formed on the inner surface of each quadrant-shaped upper portion. A converging portion 14 is formed at the insertion-sleeve-side and the body-side of the groove 13. In the converging portion 14, the depth of the groove 13 decreases gradually to zero.

No limitation is imposed on the cross-sectional shape of the lens receiving section 7 at the time when the enclosing member 5 is closed, and the lens receiving section 7 may have an elliptical cross section or a rectangular cross section when the enclosing member 5 is closed. Also, the cross-sectional shape of the grooves 13 may be changed freely. The enclosing member 5 is preferably formed from a plastic having elasticity. The base end 8b of the cylindrical holder 8 is slidably fit onto the outer circumference of the tip end portion of the body 10. The tapered front portion of the holder 8 has a tapered inner wall 12 whose diameter decreases toward the tip end of the holder 8.

Figure 3:
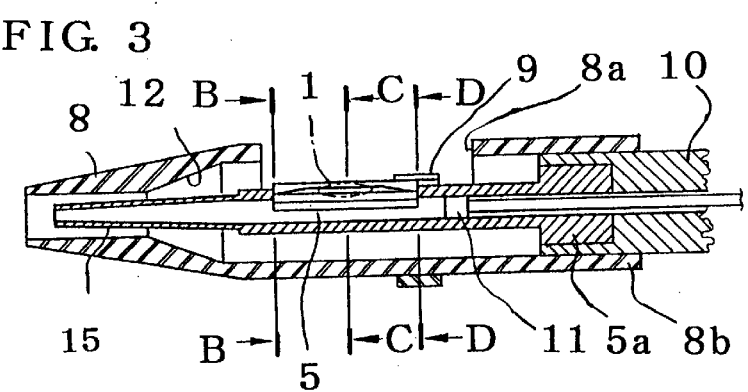
FIG. 3 is a sectional view taken along line A—A in FIG. 2.
Figure 4:
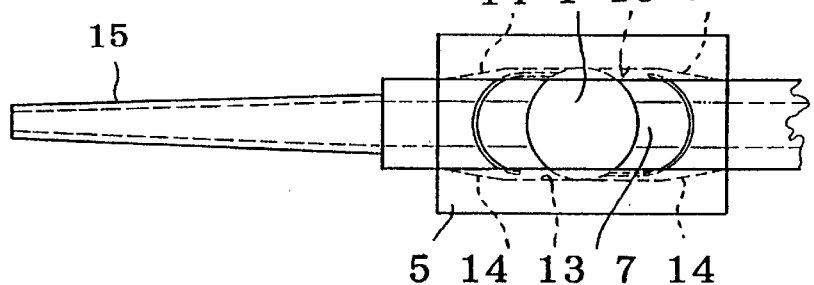
FIG. 4 is an enlarged view of a main portion of FIG. 2.

As shown in FIG. 3 and other drawings, the holder 8 has an opening 8a formed in the upper and longitudinal center portion thereof. The portion of the enclosing member 5 corresponding to the lens receiving section 7 where the hinges 6a and 6b are provided is located to face the opening 8a. The annular retainer member 9 is slidably fitted onto the enclosing member 5 and the holder 8 at the longitudinal center thereof. A cut-away portion 9a is formed in the upper portion of the retainer member 9 over the entire length thereof.

As described above, in the insertion device for a deformable intraocular lens according to the first embodiment, when the quadrant-shaped upper portions of the enclosing member 5 are opened, there is formed the lens receiving section 7 for receiving the deformable intraocular lens 1. At this time, the quadrant-shaped upper portions may be brought into an opened state by the retainer member 9 in advance. Subsequently, the deformable intraocular lens 1 is placed in the lens receiving section 7 such that the peripheral edges of the deformable intraocular lens 1 engage with the grooves 13 of the quadrant-shaped upper portions. Since the converging portions 14 are formed on the insertion-sleeve-side and the body-side of the groove 13, the deformable intraocular lens 1 can be placed while the converging portions 14 are used as a reference for positioning. In addition, since movement of the deformable intraocular lens 1 along the pushing-out direction is restricted within a range defined by the converging portions 14, the deformable intraocular lens 1 is prevented from moving within the lens receiving section 7 after placement of the deformable intraocular lens 1 immediately before insertion thereof or in advance.

Figure 5:
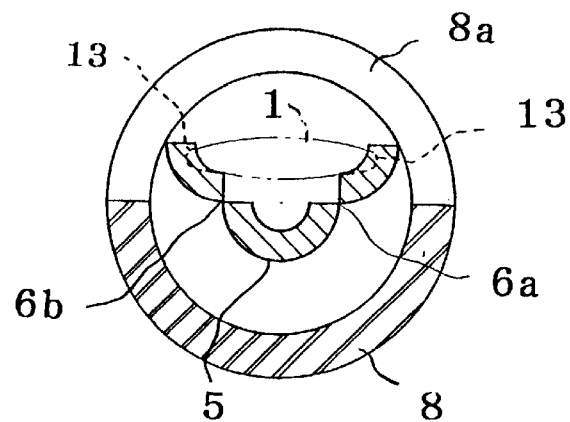
FIG. 5 is a sectional view taken along line B—B in FIG. 3.
Figure 6:
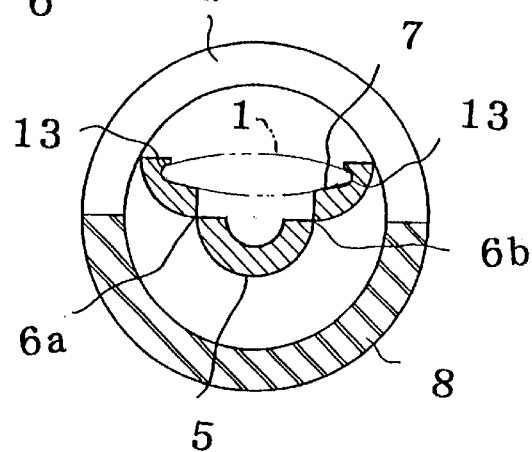
FIG. 6 is a sectional view taken along line C—C in FIG. 3.
Figure 7:
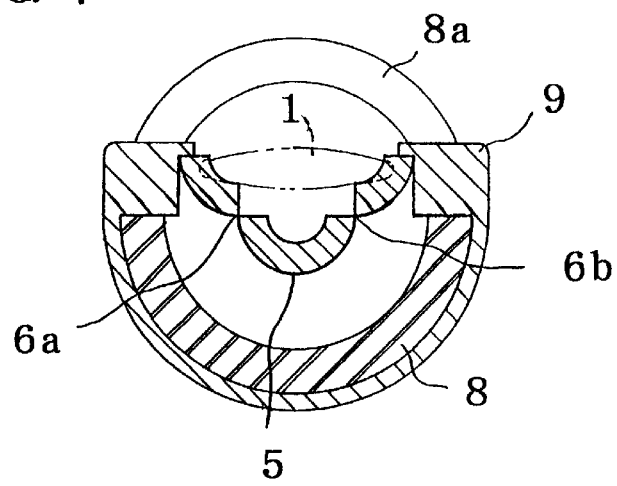
FIG. 7 is a sectional view taken along line D—D in FIG. 3.
Figure 8:
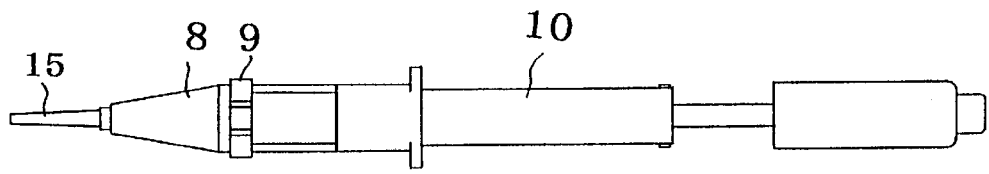
FIG. 8 is a plan view showing a state in which an intraocular lens placed in the insertion device of FIG. 1 has been deformed.
Figure 9:
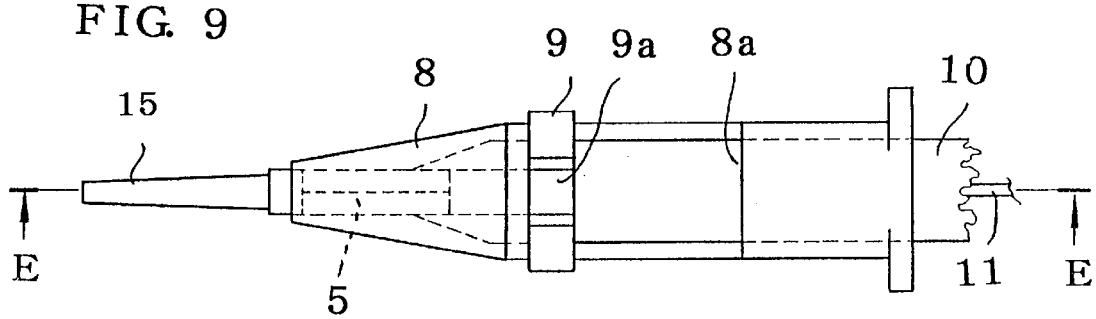
FIG. 9 is an enlarged view of a portion of FIG. 8.
Figure 10:
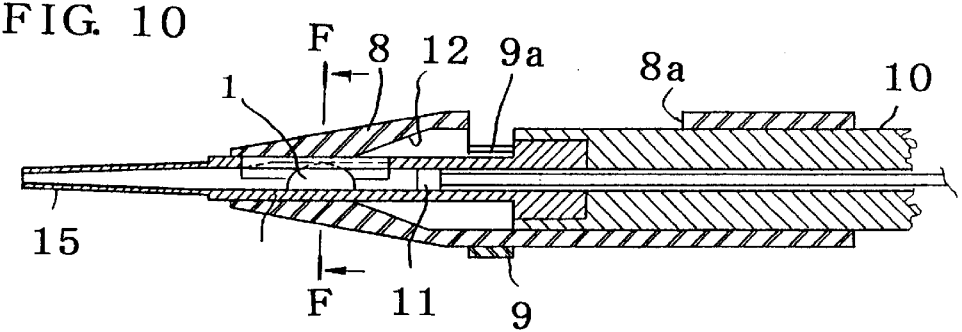
FIG. 10 is a sectional view taken along line E—E in FIG. 9.

FIGS. 5 to 7 shows cross sections respectively taken along lines B—B, C—C, and D—D in FIG. 3. As is apparent from these drawings, the grooves 13 are formed at only the portion where the deformable intraocular lens 1 is placed, and at the front and rear sides of that portion, the grooves 13 disappear due to the converging portions 14. Further, since the hinge portions 6a and 6b are provided at two circumferential positions, the hinge portions 6a and 6b do not interfere with the deformable intraocular lens 1 supported by the opposed grooves 13, and the enclosing member 5 comes into contact with the deformable intraocular lens 1 through only the peripheral edge thereof. Thus, the deformable intraocular lens 1 is held in an uncurved state in order to prevent generation of plastic deformation with time. Preferably, in order to attain a sufficient lubrication effect, before the deformable intraocular lens 1 is deformed a lubricant is applied dropwise to an inner surface of the enclosing member 5 in an area beneath the deformable intraocular lens.

Figure 11:
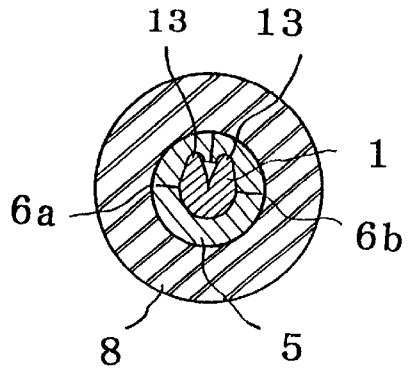
FIG. 11 is an enlarge sectional view taken along line F—F in FIG.10.

Subsequently, the holder 8 is slid toward the body 10 side, as shown in FIGS. 8 to 11. Due to this sliding movement of the holder 8, the tip ends of the quadrant-shaped upper portions opposite the hinge portions 6a and 6b come into contact with the tapered inner wall 12 of the holder 8, so that the quadrant-shaped upper portions are closed gradually. Thus, the longitudinal center portion of the enclosing member 5 where the quadrant-shaped upper portions and the hinge portions 6a and 6b exist are inserted into the smallest-inner-diameter portion of the holder 8, so that the quadrant-shaped upper portions of the enclosing member 5 are held in an closed state as shown in FIG. 11. During the above-described operation, the exterior size of the deformable intraocular lens 1 is gradually reduced to the smallest size. Subsequently, the tip end of the insertion tube 15 is inserted into the eye through an incision formed on the eyeball, and the push rod 11 is advanced. As a result, the deformable intraocular lens 1 is pushed out from the tip end of the insertion tube 15 via the interior of the insertion tube 15, which is contiguous with the lens receiving section 7, and is placed in the eye.

In the above-described embodiment, since the groove 13 provided in the lens receiving section 7 has the converging portion 14 at the insertion-tube-side and the body-side thereof, when the deformable intraocular lens 1 is placed in the lens receiving section 7, the position of the deformable intraocular lens 1 can be determined precisely. Further, since once placed the deformable intraocular lens 1 can be fixedly held within the range defined by the converging portions 14, the deformable intraocular lens 1 can be placed in the lens receiving section 7 in advance. This eliminates operation of placing the deformable intraocular lens 1 immediately before surgery. Further, the lens placed in advance can be held without causing positional shift.

Moreover, after being placed in the lens receiving section 7, the deformable intraocular lens 1 can be deformed through a simple operation; i.e., sliding of the holder 8.

Figure 12:
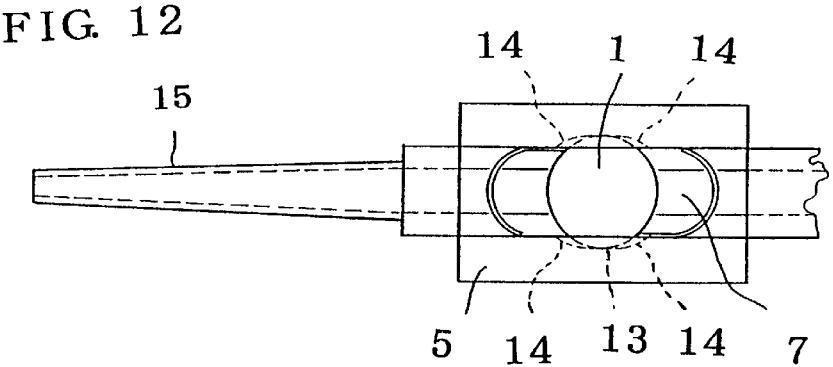
FIG. 12 is a plan view of the enclosing member of an insertion device for a deformable intraocular lens according to a second embodiment of the present invention in which grooves each have a converging portion having a different shape.
Figure 13:
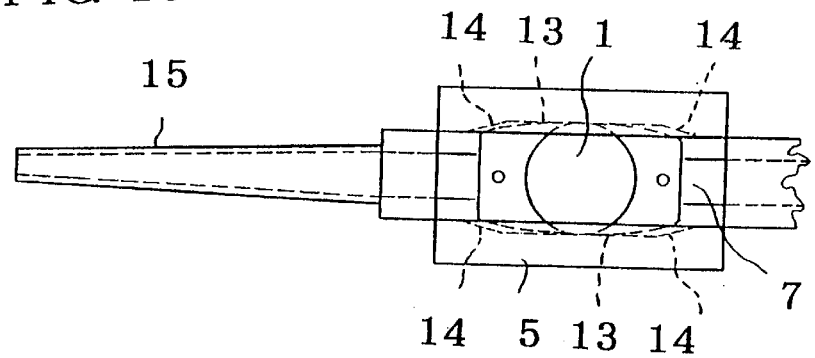
FIG. 13 is a plan view of the enclosing member of an insertion device for a deformable intraocular lens according to a third embodiment of the present invention in which grooves each have a converging portion having a different shape.
Figure 34:
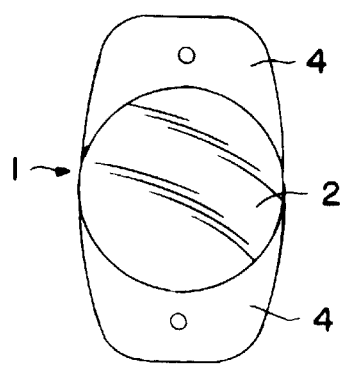
FIG. 34 is an enlarged plan view of still another deformable intraocular lens.

Next, insertion devices according to second and third embodiments of the present invention will be described with reference to FIGS. 12 and 13. In the insertion device of the second embodiment shown in FIG. 12, each of the converging portions 14 of the opposed grooves 13 has a length and shape substantially corresponding to the shape of the optical portion of the deformable intraocular lens 1 to be used. In the insertion device of the third embodiment shown in FIG. 13, each of the converging portions 14 of the opposed grooves 13 has a length and shape substantially corresponding to the shape of support portions oppositely projecting from the optical portion of the deformable intraocular lens 1, which shape is similar to that shown in FIG. 34. The structures of these embodiments allow the deformable intraocular lens 1 to be placed at the designed position more stably, so that insertion of the lens 1 into the eye can be made more reliable.

Other than the above-described features, the insertion devices of the second and third embodiments are identical to that of the first embodiment in terms of structure and operation. Therefore the reference numerals in FIGS. 12 and 13 are assigned to correspond to those used in the first embodiment.

In the above-described first through third embodiments, the enclosing member is closed and held in the closed state through sliding movement of the holder. However, this structure may be replaced with other suitable structures.

Figure 14:
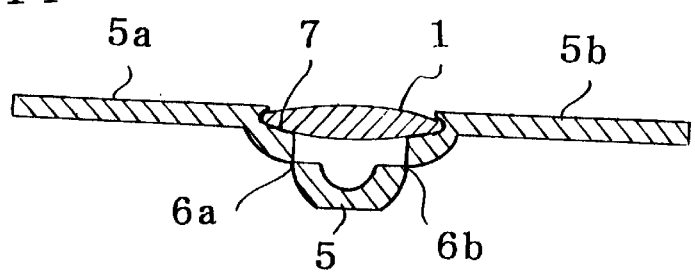
FIG. 14 is an enlarged sectional view of the enclosing member of an insertion device for a deformable intraocular lens according to a fourth embodiment of the present invention in which a lens is placed on the enclosing member in advance.
Figure 15:
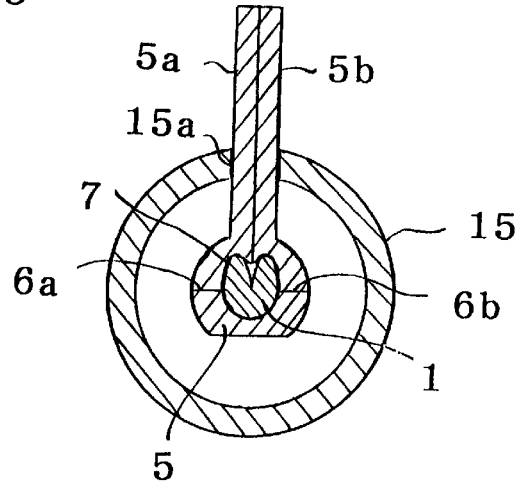
FIG. 15 is an enlarged sectional view showing a state in which the enclosing member shown in FIG. 14 is closed and held by an engagement member.

Next, an insertion device according to a fourth embodiment of the present invention will be described with reference to FIGS. 14 and 15. In FIGS. 14 and 15, numeral 5 denotes an enclosing member of the insertion device; numerals 5a and 5b denotes right and left press plates extending upward from the quadrant-shaped upper portions; numerals 6a and 6b each denote a hinge portion provided on the enclosing member 5; numeral 7 denotes a lens receiving section which is formed upon opening of the enclosing member 5 in order to receive the intraocular lens 1; and numeral 15 denotes an engagement member which is provided separately from the body and adapted to close the quadrant-shaped upper portions and hold the closed state.

That is, the enclosing member 5 of the insertion device according to the fourth embodiment differs from the enclosing member 5 having a single hinge 6 shown in FIGS. 26(a), 26(b), 27, 28(a), 28(b), and 29 in that two hinges 6a and 6b are provided at circumferential positions.

In a state where the right and left press plates 5a and 5b are open apart, the deformable intraocular lens 1 for cataract treatment is placed in the lens receiving section 7 such that the peripheral edge of the lens 1 engages the grooves 9a and 9b. Subsequently, the right and left press plates 5a and 5b are brought into contact with each other in order to reduce the exterior size of the lens 1 and hold it.

Therefore, the deformable intraocular lens 1 can be placed in the lens receiving section 7 in advance and then inserted into the eye in the same manner as in the first embodiment.

Figure 16A:
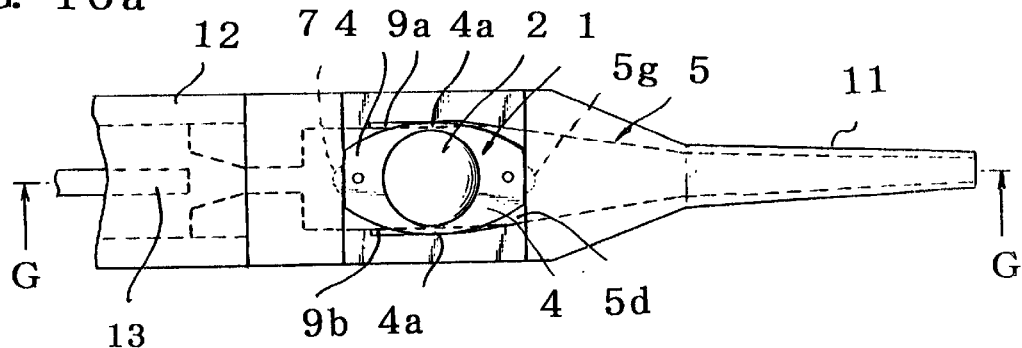
Figure 16B:
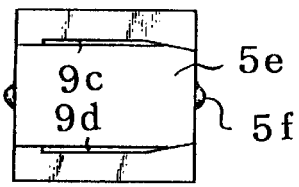
Figure 17:
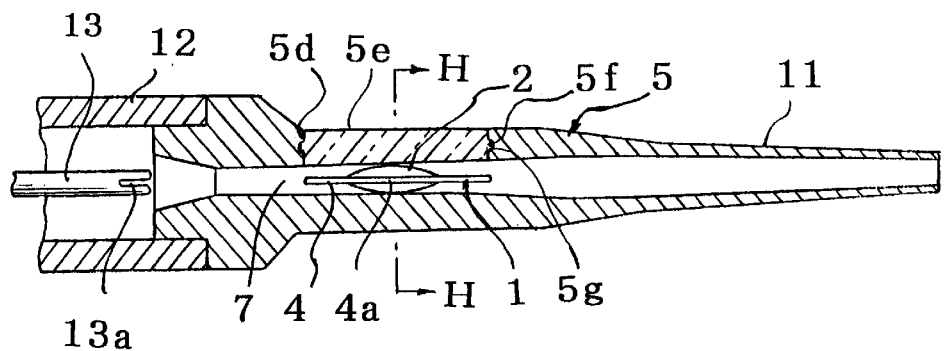
FIG. 17 is a sectional view taken along line G—G in FIG. 16 with the cap member attached.
Figure 18:
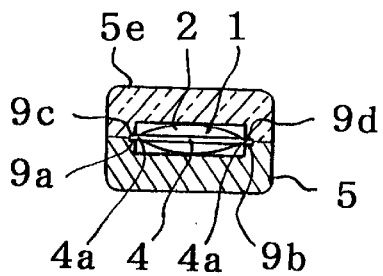
FIG. 18 is an enlarged sectional view taken along line H—H in FIG. 17.
Figure 35:
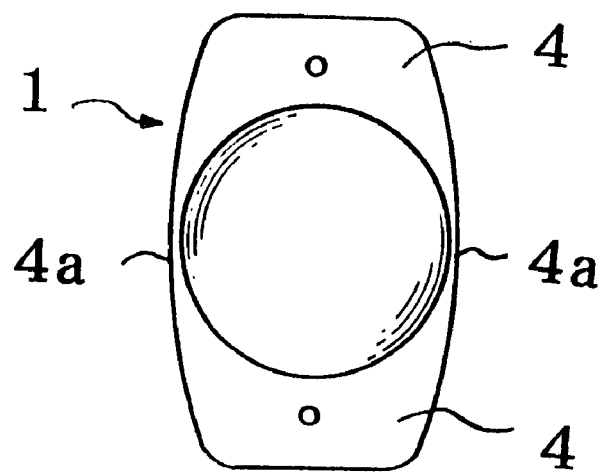
FIG. 35 is an enlarged plan view of still another deformable intraocular lens.

Next, an insertion device according to a fifth embodiment of the present invention will be described with reference to FIGS. 16(a), 16(b), 17 and 18. FIG. 16(a) is a plan view of the device with a cap member removed; and FIG. 16(b) is a bottom view of the cap member; FIG. 17 is a sectional view taken along line G—G in FIG. 16; and FIG. 18 is an enlarged sectional view taken along line H—H in FIG. 17. As shown in FIG. 35, the deformable intraocular lens 1 used in this embodiment is composed of a circular optical portion 2, a pair of thin plate-shaped support portions 4, and a peripheral edge portion 4a. The deformable intraocular lens 1 is made of an elastic material having predetermined memory characteristics. The support portions 4 are projected from the periphery of the optical portion 2 in opposite directions (vertical opposite directions in FIG. 35), and the peripheral edge portion 4a are slightly projected from the optical portion 2 rightward and leftward in FIG. 35.

Numeral 5 denotes an enclosing member for receiving the deformable intraocular lens 1, and the base portion of the enclosing member 5 is inserted and fixed to the tip end of the body 12 of the insertion device. The enclosing member 5 has a lens receiving section 7 at a longitudinal center portion thereof projected from the body 12. The enclosing member 5 has an opening 5d at the upper side of the center portion. Right and left recess grooves 9a and 9b are formed on the upper end surfaces of the enclosing member 5. A tapered insertion tube 11 is integrally formed on the front side of the lens receiving section 7. A cap member 5e which can be fitted into the opening 5d is provided as a part of the enclosing member 5. The cap member 5e has right and left recess grooves 9c and 9d on the lower end surfaces. Further, numeral 13 denotes a push rod which has a cut groove 13a at the tip end thereof.

The deformable intraocular lens 1 shown in FIG. 35 is placed into the lens setting section 7 through the opening 5d, and the cap member 5e is fitted to the opening 5d. As a result, the right and left edge portions 4a of the optical portion 2 face and engage the right and left recess grooves 9a and 9b of the enclosing member 5 and the right and left recess grooves 9c and 9d of the cap member 5e in such a manner that the optical portion 2 of the deformable intraocular lens 1 substantially does not contact the enclosing member 5 including the cap member 5e.

In the fifth embodiment, after the cap member 5e is removed from the opening 5d to allow an operator to observe the deformable intraocular lens 1, a lubricant is applied dropwise to an area beneath the lens 1 and to the inner surface of the cap member 5e, and the cap member 5e is fitted to the opening 5d to close the opening 5d. Subsequently, the push rod 13 is advanced so that the rear support portion 4 of the deformable intraocular lens 1 is received by the cut groove 13a formed at the tip of the push rod 13, and is advanced further in order to advance the deformable intraocular lens 1. When the deformable intraocular lens 1 passes through the tapered inner wall portion of the enclosing member 5, the lens 1 reaches in the vicinity of the tip end of the insertion tube 11, while the exterior size of the lens 1 is reduced gradually. In this state, the tip end of the insertion tube 11 is inserted into an incision formed on the eyeball, and the push rod 13 is further advanced to insert the lens 1 into the eye.

Except the above-described features, the insertion devices of the fifth embodiment is substantially identical to that of the first embodiment in terms of structure and operation. Therefore, the deception therefor will be omitted.

Although not illustrated in the drawings, the cap member 5e may be connected to the enclosing member 5 such that the opening 5d can be opened and closed through swing motion of the cap member 5e. Further, a structure shown in FIG. 18 may employed. That is, engagement projections 5f are projected from the front and rear surfaces of the cap member 5e, and engagement depressions 5g are formed in the front and rear walls of the opening 5d of the enclosing member 5 such that the engagement projections 5f and the engagement depressions 5g can be engaged with each other.

Further, the base portion of the enclosing member 5 may be removably attached or fixedly attached to the body 12 of the insertion device.

In the first embodiment, the holder is used to close the quadrant-shaped upper portions and to maintain the closed state. However, the first embodiment may be modified such that the quadrant-shaped upper portions are closed manually, and the closed sate is maintained through use of an engagement member.

Figure 19A:
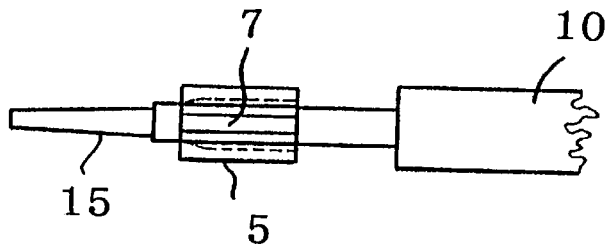
Figure 19B:
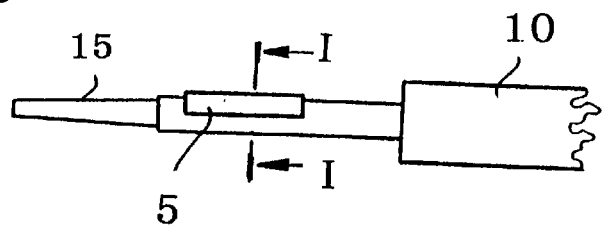
Figure 20A:
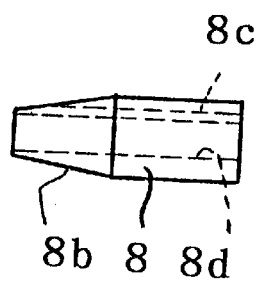
Figure 20B:
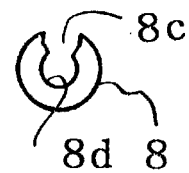
Figure 21:
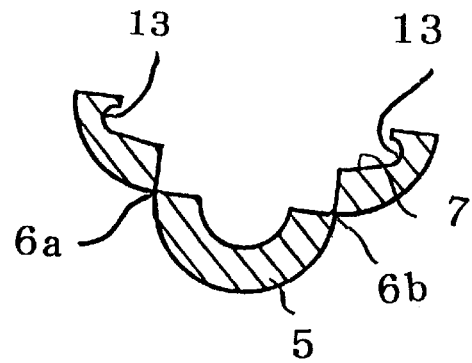
FIG. 21 is an enlarged sectional view taken along line I—I in FIG. 19(b)

Next, an insertion device according to a sixth embodiment of the present invention will be described with reference to FIGS. 19 and 21. In FIGS. 19 to 21, numeral 10 denotes a body of the insertion device; numeral 5 denotes an enclosing member of the insertion device; numerals 6a and 6b each denote a hinge portion providing on the enclosing member 5; numeral 7 denotes a lens receiving section which is formed upon opening of the enclosing member 5 in order to receive the intraocular lens 1; and numeral 8 denotes a holder which is provided separately from the body 10 and adapted to close the quadrant-shaped upper portions and hold the closed state.

The holder 8 has a tapered outer surface at the tip end thereof, and a slit 8c is formed in the upper portion of the holder 8 over the entire length thereof. Further, at the center of the holder 8 is formed a through hole 8d through which an unillustrated push rod is inserted. The retainer member used in the first embodiment is omitted. Since the members other than the above-described members are identical to those of the first embodiment, the descriptions therefor will be omitted.

Figure 22:
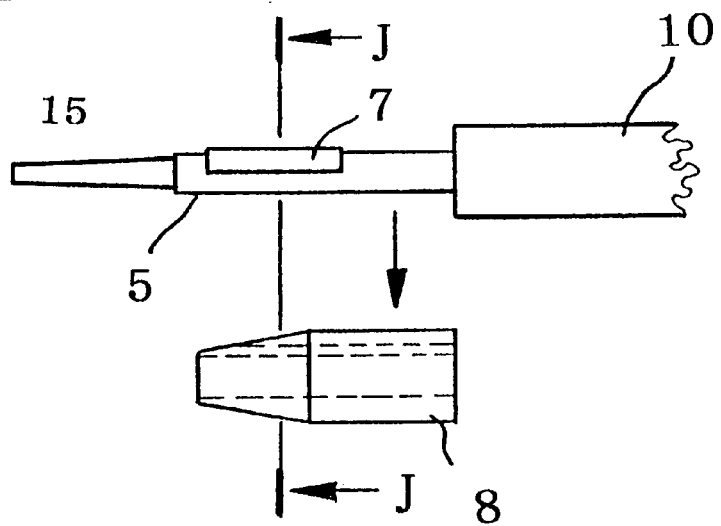
FIG. 22 is a side view showing a method of fitting the enclosing member into the holder.
Figure 23:
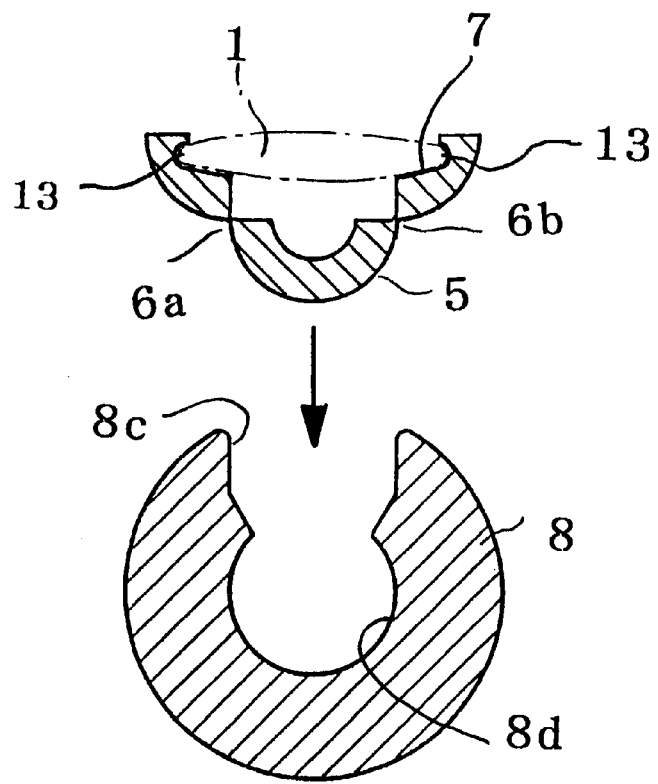
FIG. 23 is an enlarged sectional view taken along line J—J in FIG. 22.
Figure 24:
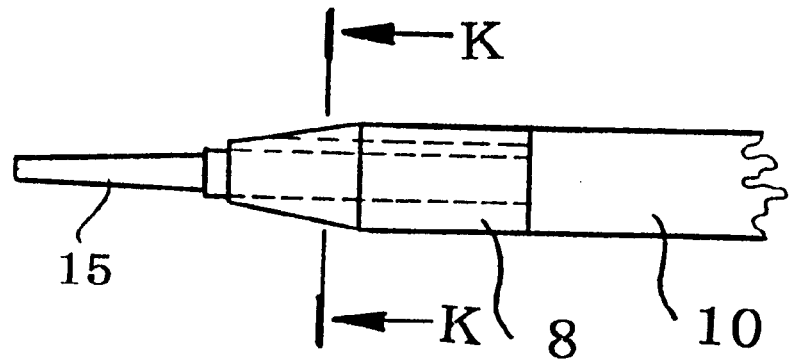
FIG. 24 is a side view showing a state in which the enclosing member has been fitted into the holder.
Figure 25:
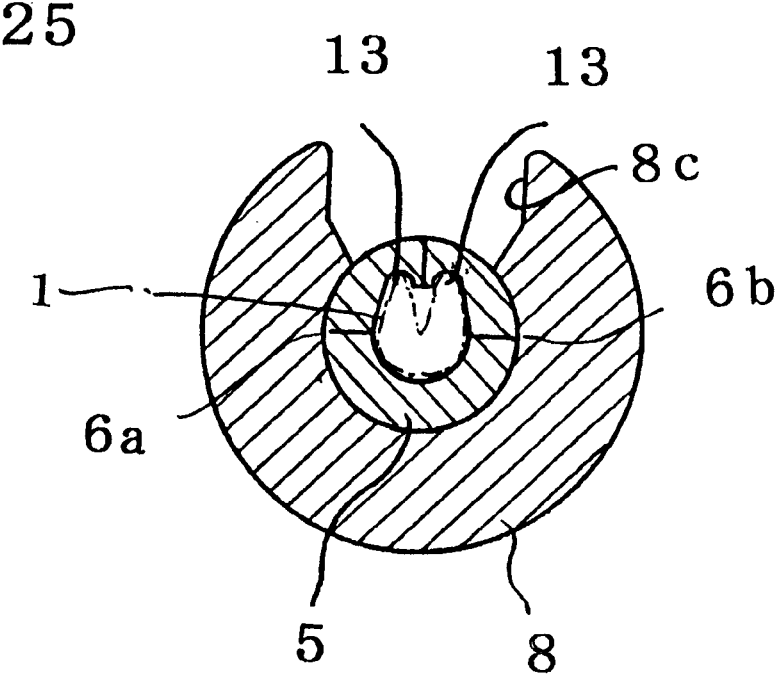
FIG. 25 is a sectional view taken along line K—K in FIG. 24.
Figure 26A:
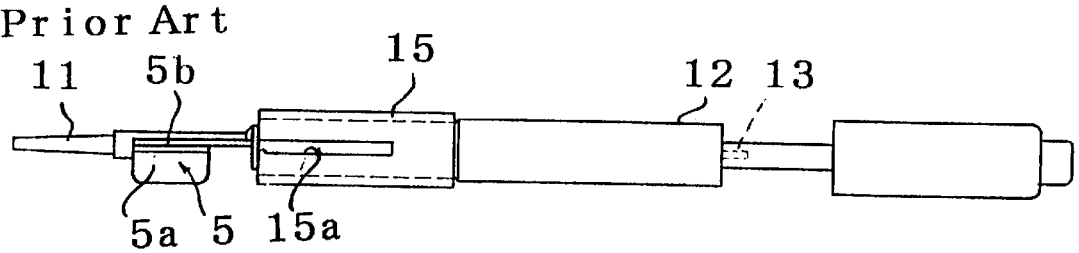
Figure 26B:
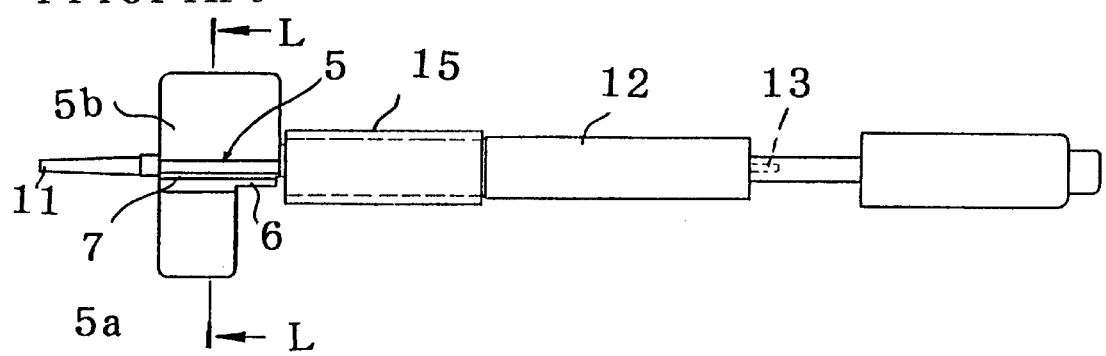
FIG. 26(b) is a side view of the device.
Figure 27:
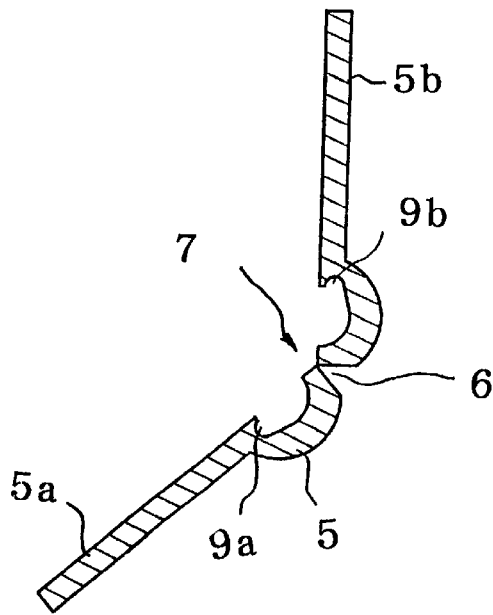
FIG. 27 is an enlarged sectional view taken along line L—L in FIG. 26(b)
Figure 28A:
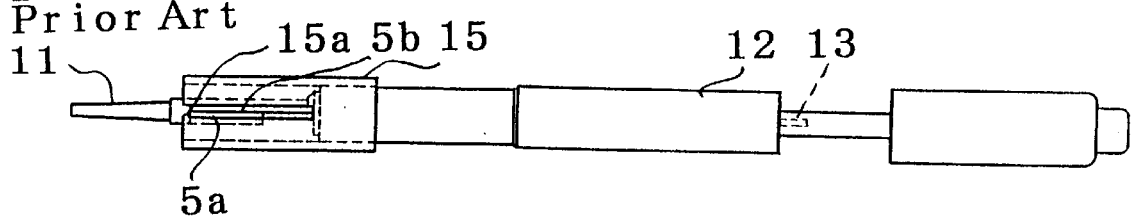
Figure 28B:
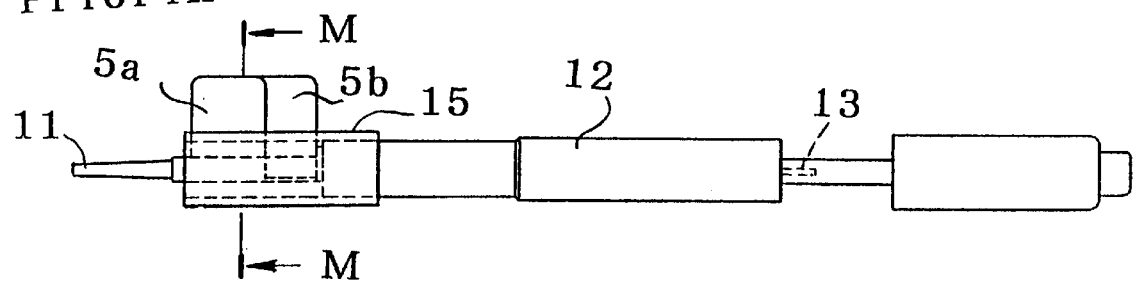
Figure 29:
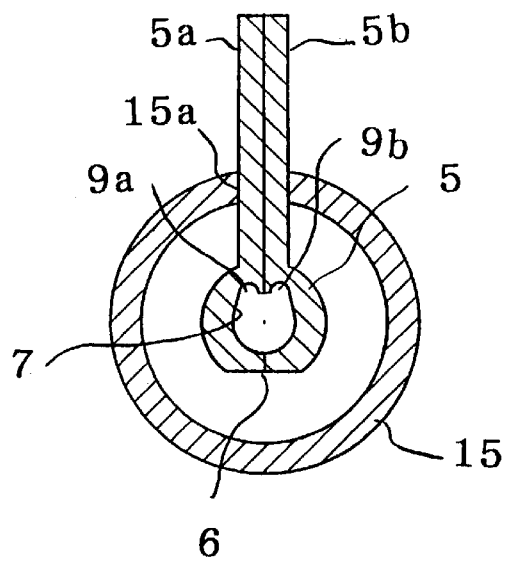
FIG. 29 is an enlarged sectional view taken along line M—M in FIG. 28(b)
Figure 30:
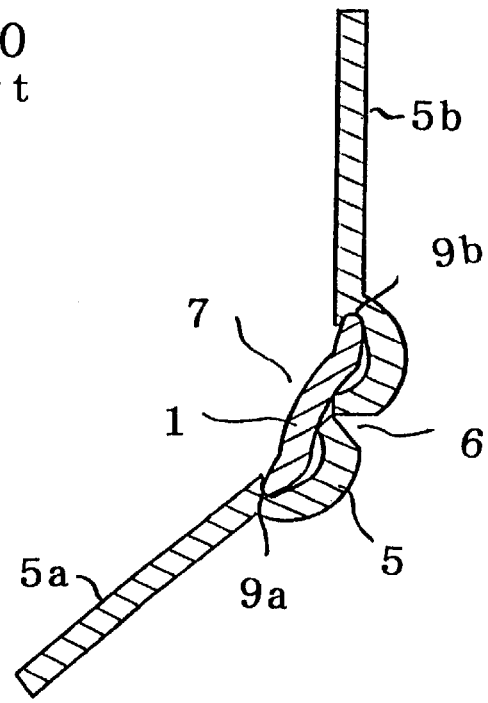
FIG. 30 is an enlarged sectional view showing a state in which a deformable intraocular lens is placed on the lens receiving section of the insertion device of FIG. 26.
Figure 31:
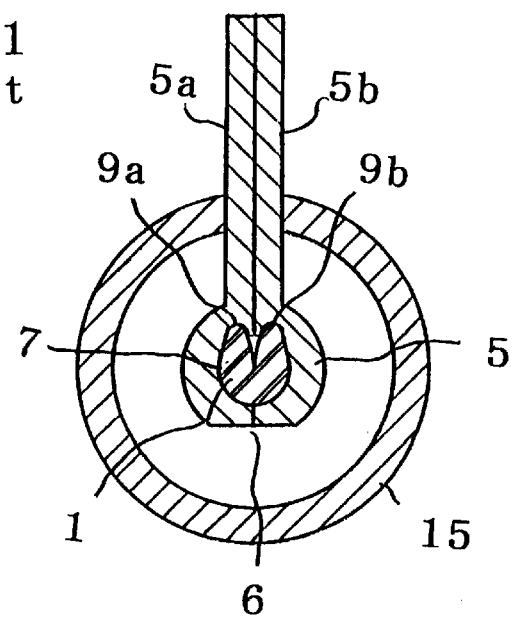
FIG. 31 is an enlarged sectional view showing a state in which the enclosing member shown in FIG. 30 is closed and held by an engagement member.
Figure 32:
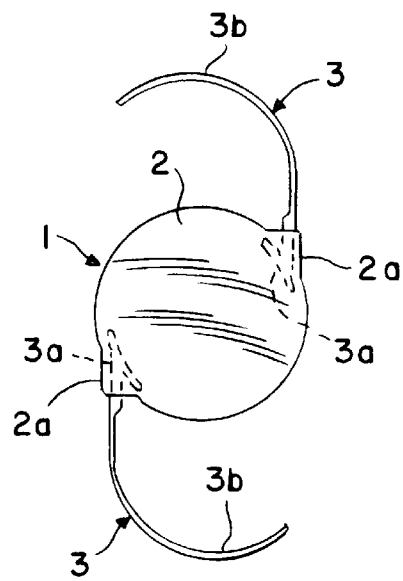
FIG. 32 is an enlarged plan view of a deformable intraocular lens.
Figure 33:
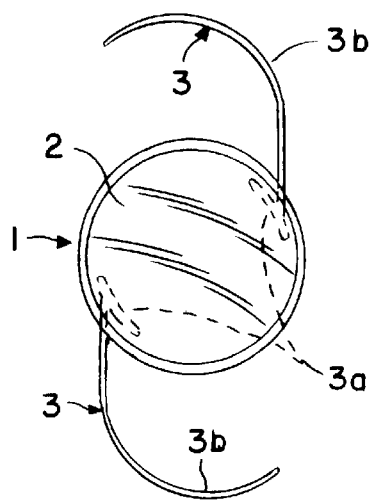
FIG. 33 is an enlarged plan view of another deformable intraocular lens.

In the insertion device according to the sixth embodiment having the above-described structure, when the quadrant-shaped upper portions of the enclosing member 5 is opened, the lens receiving section 7 is formed on the enclosing member 5. Subsequently, the deformable intraocular lens 1 is placed in the lens receiving section 7. In order to obtain sufficient lubrication effect, a lubricant or the like is preferably applied to the lens receiving section 7. Subsequently, the enclosing member 5 into which the deformable intraocular lens 1 is placed is fitted into the holder 8 as shown in FIGS. 22 and 23. Thus, the enclosing member 5 is accommodated within the holder 8, and is maintained in a completely closed state as shown in FIG. 24 and 25.

Through the above-described operation, the exterior size of the deformable intraocular lens is reduced. Since the size of the deformable intraocular lens can be reduced through the operation of fitting the enclosing member into the holder, the operation is very easy.

In the sixth embodiment, the enclosing member and the holder are preferably formed of a transparent material such as a transparent resin. In this case, since the state of the deformed intraocular lens can be checked, the degree of safety is increased.

In each of other embodiments, the enclosing member and the holder or the engagement member are preferably formed of a transparent material such as a transparent resin. In this case, since the state of the deformed intraocular lens can be checked, the degree of safety is increased.

In the case where the enclosing member is formed of a transparent material such as a transparent resin and the holder is formed of an opaque material such as metal or opaque resin, an opening serving as an observation window may be formed in the holder in order to allow an operator to check the state of the deformed intraocular lens. In this case as well, the degree of safety is increased.

In the first to fourth and sixth embodiments, the enclosing member has two hinges. However, a larger number of hinge portions may be provided. The above-describe benefits of the present invention can be attained in this case as well.

In the above-described embodiments, the holder is an independent part. However, there can be employed a structure in which the holder is integrally built in the body of the insertion device. Also, the enclosing member having hinge portions may be formed as an independent part. Further, there can be employed a structure in which the holder and the enclosing member having hinge portions are integrated together and are independent of the body of the insertion device.

In the above-described embodiments, descriptions have been given of the case where a deformable intraocular lens for cataract treatment is inserted into the eye. However, the present invention can be applied to the case where other kinds of deformable intraocular lens such as a vision correction lens is inserted into the eye. In the above-described embodiments, the enclosing member is integral with the body of the insertion device. However, the enclosing member may have a structure that allows removable attachment of the enclosing member to the body. In this case, the enclosing member and/or the body may be repeatedly used through sterilization.

In the above-described embodiments, a push rod is employed to push out a deformable intraocular lens into the eye. However, other mechanisms may be employed to push out the deformable intraocular lens into the eye.

In the fifth embodiment, when the enclosing member is formed of a transparent material such as a transparent resin, the state of the deformed intraocular lens can be checked, so that the degree of safety is increased.

In the above-described embodiments, a deformable intraocular lens is held such that only the peripheral edge portion of the lens contacts the enclosing member. When a deformable intraocular lens having support portions projected from the optical portion with an angle is used, in addition to the structure for supporting the peripheral portion of the lens, there may be employed a structure for supporting the support portions of the lens by a part of the enclosing member or another independent member in order to maintain the angle formed between the support portions and the optical portion.

Obviously, numerous modifications and variations of the present invention are possible in light of the above teachings. It is therefore to be understood that within the scope of the appended claims, the present invention may be practiced otherwise than as specifically described herein.

What is claimed is:

1. An insertion device for inserting into the eye a deformable intraocular lens in which at least an optical portion is formed of an elastic material having predetermined memory characteristics or a deformable intraocular lens in which at least an optical portion is formed of an elastic material having predetermined memory characteristics and which has a supporting portion for supporting the optical portion within the eye, wherein said insertion device comprises an enclosing member for receiving and holding the deformable intraocular lens in an enclosed manner, said enclosing member having a plurality of hinge portions.

2. An insertion device for inserting into the eye a deformable intraocular lens in which at least an optical portion is formed of an elastic material having predetermined memory characteristics and which has a supporting portion made of a material different from that of the optical portion and adapted to support the optical portion within the eye, wherein said insertion device comprises an enclosing member for receiving and holding the deformable intraocular lens in an enclosed manner, said enclosing member having a plurality of hinge portions.

3. An insertion device for a deformable intraocular lens according to claim 1, wherein said deformable intraocular lens is placed in said enclosing member in advance.

4. An insertion device for inserting into the eye a deformable intraocular lens in which at least an optical portion is formed of an elastic material having predetermined memory characteristics or a deformable intraocular lens in which at least an optical portion is formed of an elastic material having predetermined memory characteristics and which has a supporting portion for supporting the optical portion within the eye, said insertion device comprising:

(a) an enclosing member for receiving and holding the deformable intraocular lens in an enclosed manner, wherein said enclosing member has two or more hinge portions that allows said enclosing member to be closed in order to deform the deformable intraocular lens; and (b) a holder for closing said enclosing member and maintaining the closed state.

5. An insertion device for a deformable intraocular lens according to claim 4, wherein said enclosing member having said hinge portions has grooves on the inner surface in order to receive and hold the deformable intraocular lens.

6. An insertion device for a deformable intraocular lens according to claim 4, wherein said enclosing member having said hinge portions and said holder are integrally built in a body of the insertion device.

7. An insertion device for a deformable intraocular lens according to claim 4, wherein said enclosing member having said hinge portions is an independent part.

8. An insertion device for a deformable intraocular lens according to claim 4, wherein said holder is an independent part.

9. An insertion device for a deformable intraocular lens according to claim 4, wherein said enclosing member having said hinge portions and said holder are integrated together and are separated from a body of the insertion device.

10. An insertion device for a deformable intraocular lens according to claim 4, wherein said enclosing member having said hinge portions and said holder are transparent.

11. An insertion device for a deformable intraocular lens according to claim 4, wherein said enclosing member having said hinge portions is transparent and said holder has an opening serving as an observation window.

12. An insertion device for inserting into the eye a deformable intraocular lens in which at least an optical portion is formed of an elastic material having predetermined memory characteristics or a deformable intraocular lens in which at least an optical portion is formed of an elastic material having predetermined memory characteristics and which has a supporting portion for supporting the optical portion within the eye, said insertion device comprising:

(a) an enclosing member for receiving and holding the deformable intraocular lens in an enclosed manner, said enclosing member having at least one hinge portion that allows said enclosing member to be closed in order to deform the deformable intraocular lens;

(b) a holder for closing said enclosing member and maintaining the closed state; and (c) a retainer member for maintaining said enclosing member having said at least one hinge portion in an opened sate when the deformable intraocular lens is placed in said enclosing member.

\* \* \* \* \*